US005750773A

United States Patent [19]
Bowden

[11] Patent Number: 5,750,773
[45] Date of Patent: May 12, 1998

[54] PROCESS FOR PREPARING 4,4,4-TRICHLOROBUTYL ACETATE

[75] Inventor: Martin Charles Bowden, Huddersfield, United Kingdom

[73] Assignee: Zeneca Limited, London, England

[21] Appl. No.: 678,273

[22] Filed: Jul. 11, 1996

[30] Foreign Application Priority Data

Jul. 17, 1995 [GB] United Kingdom ............... 9514564

[51] Int. Cl.$^6$ .................................................. C07C 69/63
[52] U.S. Cl. .................................................. 560/226
[58] Field of Search ........................................ 560/226

[56] References Cited

U.S. PATENT DOCUMENTS 4,053,380  10/1977  Fujita et al. .................. 204/163 R

FOREIGN PATENT DOCUMENTS 2307783  11/1976  France .
1109662   6/1961   Germany .
871836    7/1961   United Kingdom .

OTHER PUBLICATIONS

B. Ameduri et al., "Synthesis of Chllorinated . . . Telogens". Macromolecules, vol. 24, pp. 2475–2484, Apr. 1991.

Ameduri et al., *Macromolecules*, vol. 24, p. 2475 (1991).

Primary Examiner—Gary Geist
Assistant Examiner—Rosalynd Keys
Attorney, Agent, or Firm—Joel G. Ackerman

[57] ABSTRACT

A process for the preparation of 4,4,4-trichlorobutyl acetate comprising reacting allyl acetate with chloroform in the presence of a radical initiator, characterized by the incremental addition of the allyl acetate to the chloroform.

9 Claims, No Drawings

PROCESS FOR PREPARING 4,4,4-TRICHLOROBUTYL ACETATE

The present invention relates to an improved process for preparing 4,4,4-trichlorobutyl acetate by reacting allyl acetate with chloroform. 4,4,4-Trichlorobutyl acetate is an important intermediate and product in the chemical industry.

The synthesis of telogens by telomerization of allyl acetate with chloroform by the all-in addition of the allyl acetate to the chloroform at the start of the reaction is disclosed in *Macromolecules* 1991, 24, 2475–2484. The reaction scheme for this reaction is as follows

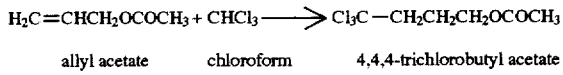

| allyl acetate | chloroform | 4,4,4-trichlorobutyl acetate |

It was found that even with a large excess of the telogen, chloroform, the reaction product mixture contains significant quantities of the diadduct (or "bis" product, he) and triadduct (or "tris" product, III)

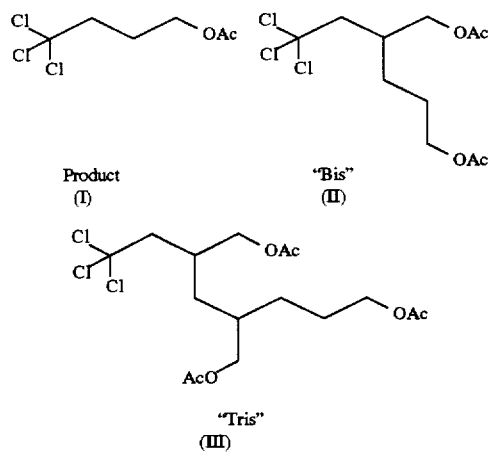

at the expense of high yields of the desired product, 4,4,4-trichlorobutyl acetate (I). It is further reported that such a phenomenon is rat her normal with reference to the radical telomerization of allyl acetate with methyl trichloroacetate and methyl dichloroacetate.

We have now found an improved process for preparing 4,4,4-trichlorobutyl acetate which overcomes the low yield problem of the prior art process.

According to the present invention there is provided a process for the preparation of 4,4,4-trichlorobutyl acetate comprising reacting ally acetate with chloroform in the presence of at least one radical initiator, characterised by the incremental addition of the allyl acetate to the chloroform over the period of the reaction. The term "incremental addition" as used herein includes both addition of separate aliquots and also a continuous stream of allyl acetate.

We have found that surprisingly the process of present invention provides a substantially improved yield of the monoadduct, namely 4,4,4-trichlorobutyl acetate, over the prior art process by suppressing the co-production of oligomeric by-products.

In one preferred embodiment of the present invention, the allyl acetate may added to the reaction mixture in two or more aliquots over the period of the reaction. Preferably there are three or more additions of the allyl acetate, more preferably four or more additions, even more preferably eight or more additions. Nevertheless significant yield benefits may be obtained with less than eight separate additions. It will be appreciated that the allyl acetate can be added at either regular or non-regular intervals, and it is not necessary that the same amount of allyl acetate be added each time. The addition of the second and subsequent aliquots preferably takes place after intervals of at least one hour following the previous addition.

In an especially preferred embodiment of the present invention, the allyl acetate is continuously fed to the reaction mixture at a controlled rate. This can conveniently be achieved using pump feeding equipment. The rate of addition may be varied over the course of the reaction which may be monitored by sampling and determining the rate of formation of the desired product by the use of gas chromatography.

Preferably, the chloroform is always present in excess with the overall molar ratio of allyl acetate to chloroform being less than one. Preferably the overall molar ratio of allyl acetate to chloroform is at least 1:5, even more preferably it is within the range 1:10 to 1:15.

The reaction is preferably conducted at elevated pressure, preferably in the range of about 80 psi to about 90 psi. The reaction can be conveniently conducted in a pressure reactor. The reaction is also preferably carried out at elevated temperature, preferably within a temperature range of 100°–150° C., and a temperature of about 120° C. is particularly preferred.

Many radical initiators are known and any convenient radical initiator may be used. Preferred initiators include organic peroxides such as di acyl peroxides, eg benzoyl peroxide, and dialkyl peroxides, eg. t-butyl peroxide (TPO), and azo compounds, eg azobisisobutyronitrile (AIBN). Particularly favourable results may be obtained when a peroxide and an azo compound, eg TPO and AIBN, are used in combination. All the initiator(s) may be added to the chloroform at the start of the process, or may also be added in a incremental manner, preferably in admixture with the allyl acetate.

The period of the reaction may extend from about 3 hours to about 48 hours, depending upon the volume of react ants and the temperature and pressure used. Generally a period of from about 5 to about 15 hours is sufficient.

Various further preferred features and embodiments of the present invention will now be described with reference to the following non-limiting examples:

EXAMPLE 1

This Example illustrates the preparation of 4,4,4-trichlorobutyl acetate in accordance with the process of the present invention The details of the reactants are set out below in Table 1:

TABLE 1

| Material | Act. Wt. (g) | Strength (%) | MW | Moles | Mol/Mol |
|---|---|---|---|---|---|
| Allyl acetate | 6.88 | 99 | 100 | 0.069 | 1 |
| Chloroform | 82.1 | 99 | 119 | 0.69 | 10 |
| t-butyl peroxide | 0.5 | 98 | 146 | 0.003 | 0.05 |
| AIBN | 0.3 | 97 | 164 | 0.002 | 0.03 |

Chloroform (82.1 g), allyl acetate (0.86 g), t-butyl peroxide (0.063 g) and AIBN (0.038 g) were charged to a 100 ml Hasteloy C Parr pressure reactor. The reactor was sealed and heated with agitation to 120° C. and 80 psi, then held at this temperature for 1 hour. After this time, the reactor was cooled and second aliquots of allyl acetate (0.86 g), t-butyl peroxide (0.063 g) and AIBN (0.038 g) were added. The reactor was resealed and again heated at 120° C. for 1 hour. This procedure was repeated so that a total of eight additions were made. After eight complete cycles, the reaction was agitated at 120° C. for a further 1.5 hours before cooling to room temperature. The composition of the unpurified product mixture was determined by gas chromatography (peak area) as I:II:III=80:20:0

The reaction mass was concentrated by rotary evaporation, and the crude product then distilled under reduced pressure (70°–74° C. at 3 mmHg) to give the desired product (8.0 g) in 53% yield.

1Hnmr (CDCL$_3$): 2.10 (s,3H,CH$_3$CO$_2$); 2.15 (m,2H,CH$_2$); 2.80 (m,2H,CH$_2$CCl$_3$); 4.15 (CH$_2$OAc). MS: 158 (M$^+$—AcOH). IR: 1750 (C=O).

For the purpose of comparison the preparation of 4,4,4-trichlorobutyl acetate using the all-in process of the prior art was carried out with identical quantities of reactants as set out in Table 1 above as follows.

Chloroform (82.1 g), allyl acetate (6.88 g), t-butyl peroxide (0.3 g) and AIBN (0.3 g) were charged to a 100 ml Hasteloy C Parr pressure reactor. The reactor was sealed and heated with agitation to 120° C., then held at this temperature for 5.5 hours. After this time, the reactor was cooled and GC analysis indicated that complete consumption of allyl acetate had occured. The composition of crude product mixture (GC area) was I:II:III=42:40:12.

The reaction mass was concentrated by rotary evaporation, and the crude product then distilled under reduced pressure (70°–74° C. at 3 mmHg) to give the desired product (3.0 g) in 20% yield.

The process of the present invention therefore gives a demonstrable significant yield enhancement improvement over the prior art process, of 33% (from 20% to 53%).

The results of Example 1 can also be instructively compared with the results quoted in *Macromolecules* supra. This describes an all-in process in which chloroform, allyl acetate, t-butyl peroxide and AIBN were charged to a Pfaudler vessel and stirred at 120° C. for 15 hours. Products were isolated by distillation. Details of the reactants are given below in Table 2

TABLE 2

| Material | MW | Mol/Mol |
|---|---|---|
| Allyl acetate | 100 | 1 |
| Chloroform | 119 | 10 |
| t-butyl peroxide | 146 | 0.05 |
| AIBN | 164 | 0.03 |

The composition of the product mixture is given as allyl acetate(I); "bis" oligomer(II): "tris" oligomer(III)=44:40:16. This is very similar to the result obtained above, and is a further confirmation that the process of the present invention gives an improved yield of the desired product as compared with the prior art process.

EXAMPLE 2

This example further illustrates the improved yield given by the process of the present invention, and also illustrates the preferred chloroform:allyl acetate ratios. Details of the reactants and the results are given below in Table 3 in which Experimental Runs A and B exemplify the prior art process and C and D represent the invention process.

TABLE 3

| Run | Number of Aliquots | Reactant Ratio Chloroform/AA | Product Mixture (I:II:III) | Isolated Yield of I (%) |
|---|---|---|---|---|
| A | 1 | 10:1 | 42:40:12 | 20 |
| B | 1 | 5:1 | 15:29:24 | 13 |
| C | 4 | 10:1 | 48:26:5 | 40 |
| D | 3 | 13:1 | 58:19:3 | 50 |

EXAMPLE 3

This Example illustrates the process of the invention in which the allyl acetate is added in a semi-continuous operation.

| Material | Weight (g) | Strength (%) | 100% wt | Mol. Wt | Mole | Mole ratio |
|---|---|---|---|---|---|---|
| Allyl acetate | 261 | 99 | 259 | 100 | 2.59 | 1.0 |
| Chloroform | 3117 | 99 | 3087 | 119 | 25.9 | 10 |
| t-Butyl peroxide | 19 | 98 | 19 | 146 | 0.13 | 0.05 |
| AIBN | 13 | 97 | 13 | 164 | 0.08 | 0.03 |

A 3 liter stainless steel Buchi reactor was fitted with an HPLC pump and recirculation heater. To this was charged chloroform (1462 ml), the vessel was sealed and the contents heated to 130° C. A solution in chloroform (105 ml) of t-butyl peroxide (2.4 ml) and AIBN (1.3 g) was charged to the reactor by HPLC pump over 10 minutes. A solution in chloroform (209 ml) of allyl acetate (141 ml), t-butyl peroxide (9.7 ml) and AIBN (5.2 g) was then charged by HPLC pump over 5 hr, maintaining the temperature at 130° C. The reaction mass was allowed to self-cool then stood at ambient overnight. The mixture was reheated to 130° C., then the two allyl acetate/chloroform/t-butyl peroxide/AIBN charges outlined above were repeated exactly. The mixture was agitated at 130° for 2 hr after completion of reagent addition, then the reactor was allowed to self-cool to ambient and again stood overnight. The reaction mass was removed from the reactor and concentrated by rotary evaportion to give the crude product (664 g, 70% crude yield). Distillation (66°–68° C. @ 2 mbar) allowed separation of oligomeric impurities to give the product as a colurless oil (67% yield).

$^1$Hnmr (CDCl$_3$): 2.10 (s, 3H, CH$_3$CO$_2$), 2.10–2.25 (m, 2H, CH$_2$), 2.75–2.90 (m, 2H, CH2CCl3), 4.15 (t, 2H, CH2OAc). GCMS: 158 (M$^+$-HOAc), 121, 109, 87, 73, 43. IR: 1750.

I claim:

1. A process for the preparation of 4,4,4-trichlorobutyl acetate comprising reacting allyl acetate with chloroform in the presence of a radical initiator, characterized by the incremental addition of the allyl acetate to the chloroform.

2. A process according to claim 1 wherein the incremental addition is achieved by the addition of separate aliquots of allyl acetate over the period of the reaction.

3. A process according to claim 1 wherein the incremental addition is achieved by the continuous addition of the allyl acetate to the chloroform over the period of the reaction.

4. A process according to claim 1 conducted under elevated pressure and elevated temperature conditions.

5. A process according to claim 4 conducted at a pressure within the range 80 to 90 psi.

6. A process according to claim 4 conducted at a temperature within the range 100°–150° C.

7. A process according to claim 1 wherein the radical initiator is selected from an organic peroxide and an azo compound.

8. A process according to claim 7 wherein the radical initiator is selected from t-butyl peroxide, azobisisobutyronitrile and mixtures thereof.

9. A process according to claim 1 wherein the overall molar ratio of chloroform to allyl acetate is within the range 10:1 to 15:1.

* * * * *